United States Patent [19]

Harper

[11] Patent Number: 5,240,836
[45] Date of Patent: Aug. 31, 1993

[54] METHYLATION OF ORGANIC COMPOUNDS

[75] Inventor: David B. Harper, Lisburn, Ireland

[73] Assignee: The Queens University of Belfast, Ireland

[21] Appl. No.: 613,539

[22] PCT Filed: May 24, 1989

[86] PCT No.: PCT/GB89/00575
§ 371 Date: Nov. 23, 1990
§ 102(e) Date: Nov. 23, 1990

[87] PCT Pub. No.: WO89/11535
PCT Pub. Date: Nov. 30, 1989

[30] Foreign Application Priority Data

May 25, 1988 [GB] United Kingdom .............. 8812419
Jun. 24, 1988 [GB] United Kingdom .............. 8815143

[51] Int. Cl.$^5$ .......................... C12P 1/02; C12P 7/62; C12P 7/22; C12P 11/00

[52] U.S. Cl. .................................. 435/130; 435/156; 435/171; 435/135

[58] Field of Search ................. 435/156, 135, 172.3, 435/171

[56] References Cited

PUBLICATIONS

Harper, Science, 315: 55–57 (1985).
Harper et al., J. Gen. Microbiol., 132: 1231–1246 (1986).
Harper et al., J. Gen. Microbiol., 134: 2831–2839 (1988).

*Primary Examiner*—Richard A. Schwartz
*Assistant Examiner*—Nancy T. Vogel
*Attorney, Agent, or Firm*—Salter, Michaelson & Benson

[57] ABSTRACT

A method of O-methylation of a phenol, S-methylation of a thiophenal, or methylesterification of a carboxylic acid is disclosed, which involves contacting the phenol, thiophenol, or carboxylic acid with a halomethane in the presence of a fungus selected from the group consisting of Hymenochaetaceae, Polyporaceae, and Corticiaceae.

5 Claims, No Drawings

METHYLATION OF ORGANIC COMPOUNDS

This invention relates to methylation of organic compounds.

At present the industrial esterification of carboxylic acids to form the methyl ester is normally effected by refluxing the carboxylic acid with methanol in the presence of mineral acid and separating the ester from the reaction mixture by fractional distillation. Methylation of phenols to form anisoles is normally performed industrially by refluxing dimethyl sulphate with the sodium salt of the phenol. The resulting anisole is separated from the reaction mixture by solvent extraction or distillation techniques. Both methylation of carboxylic acids and of phenols is therefore energy and capital intensive.

The object of the present invention is to provide a cheaper method of methylation.

According to the invention there is provided a method of methylation characterised in that an organic substance that is to be methylated is contacted with a methyl donor material in the presence of fungus or another organism into which an appropriate fungal gene is introduced.

The invention, therefore, is a biological system and it offers the possibility of preparation of methylated compounds at ambient temperatures using a gaseous halomethane. It is believed that this system is potentially cheaper to operate than the known techniques.

In a preferred embodiment of the invention a fungal preparation or immobilised enzyme preparation is produced using an appropriate fungus preferably selected from fungi which can biosynthesise chloromethane such as the Hymenochaetaceae, Polyporaceae and Corticiacae. Alternatively the invention employs an immobilised preparation of a bacteria into which a cloned copy of the fungal gene, or genes, coding for the methylation system has been introduced using standard genetic manipulation techniques. An aqueous solution of the organic substance to be methylated, for example a carboxylic acid or a phenol containing dissolved gaseous chloromethane are together cycled through the preparation. Insoluble methyl ester of the carboxylic acid or O-methyl phenol as the case may be, is formed and can be separated and the unreacted mixture recycled through the preparation. Additional starting materials can be added as necessary to the recycle stream.

The reaction is carried out at ambient temperature for example between 15° and 25° C. and preferably at a pH between 2 and 8.

The invention can be applied to a wide range of organic substances, particularly acids such as benzoic, furoic, phenylacetic, cinnamic, propionic, butyric, isobutyric, valeric, isovaleric, hexanoic and heptanoic acids and halo-, methyl and hydroxy-, methoxy- and cyano- substituted derivatives of acids.

The invention can also be applied to the methylation of many phenols and thiophenols including both halo- and methyl substituted compounds such as 2-, 3- and 4- fluorophenol, 2-, 3- and 4- chlorophenol, 2, 6- dichlorophenol, 2-, 3- and 4- bromophenol, 2-iodophenol and 2-, 3- and 4- methylphenol.

The methyl donor material may be a halo methane such as chloro-, bromo- or iodo-methane. As mentioned above a gaseous donor material is preferably used.

The following Examples further illustrate the invention.

EXAMPLE 1

The fungus *Phellinus pomaceus* (NCWRF.FPRL 33A obtained from the National Collection of Wood Rotting Fungi, Princes Risborough Laboratory, Building Research Establishment, Aylesbury, Bucks., England, or CBS 137.42 obtained from the Centraalbureau Voor Schimmelcultures, Baarn, The Netherlands, was used as a basis of the system.

A 2 mM solution of butyric acid containing 0.1 mM chloromethane buffered at pH 4.0 with 20 mM citrate buffer was incubated with 0.035 g of fungal mycelium for a period of 12 hours at a temperature of 25° C. Methyl butyrate was formed at a rate of 245 nanomoles/g fungal mycelium/hour.

EXAMPLE 2

A 0.5 mM solution of benzoic acid containing 1.23 mM chloromethane and buffered at pH 4.0 with 20 mM citrate buffer was incubated with 0.035 g of fungal mycelium (*Phellinus pomaceus*, NCWRF.FPRL 33A or CBS 137.42) for a period of 12 hours at a temperature of 25° C. Methyl benzoate was formed at a rate of 290 nanomoles/g fungal mycelium/hour.

EXAMPLE 3

A 10 mM solution of phenol containing 1.23 mM chloromethane and buffered at pH 4.0 with 20 mM citrate buffer was incubated with 0.035 g of fungal mycelium (*Phellinus pomaceus*, NCWRF. FPRL 33A or CBS 137.42) at 25° C. for 12 h. Anisole was formed at a rate of 30 nanomoles/g fungal mycelium/hour.

EXAMPLE 4

A 2 mM solution of 2-chlorophenol containing 1.23 mM chloromethane and buffered at pH 4.0 with 20 mM citrate buffer was incubated with 0.035 g of fungal mycelium (*Phellinus pomaceus*, NCWRF. FPRL 33A or CBS 137.42) at 25° C. for 12 h. 2-chloroanisole was formed at a rate of 16 nanomoles/g fungal mycelium/hour.

EXAMPLE 5

A 1 mM solution of thiophenol containing 1.23 mM chloromethane and buffered at pH 4.0 with 20 mM citrate buffer was incubated with 0.035 g of fungal mycelium (*Phellinus pomaceus*, NCWRF. FPRL 33A or CBS 137.42) at 25° C. for 12 h. Thioanisole was formed at a rate of 113 nanomoles/g fungal mycelium/hour.

EXAMPLE 6

The fungus *Phellinus ribis* (NCWRF. FPRL 42 obtained from the National Collection of Wood Rotting Fungi, Princes Risborough Laboratory, Building Research Establishment, Aylesbury, Bucks or CBS 175.29 obtained from the Centraalbureau voor Schimmelcultures, Baarn, The Netherlands) was used as a basis of the system.

A 2 mM solution of butyric acid containing 0.2 mM chloromethane buffered at pH 4.0 with 20 mM citrate buffer was incubated with 0.035 g of fungal mycelium for a period of 15 hours at a temperature of 25° C. Methyl butyrate was formed at a rate of 197 nanomoles/g fungal mycelium/hour.

EXAMPLE 7

A 0.5 mM solution of benzoic acid containing 0.2 mM chloromethane and buffered at pH 4.0 with 20 mM citrate buffer was incubated with 0.035 g of fungal mycelium (*Phellinus ribis* NCWRF. FPRL 42 or CBS 175.29) for a period of 15 hours at a temperature of 25° C. Methyl benzoate was formed at a rate of 77 nanomoles/g fungal mycelium/hour.

EXAMPLE 8

A 2 mM solution of phenol containing 0.2 mM chloromethane and buffered at ph 4.0 with 20 mM citrate buffer was incubated with 0.035 g of fungal mycelium (*Phellinus ribis* NCWRF. FPRL 42 or CBS 175.29) at a temperature of 25° C. for a period of 15 hours. Anisole was formed at a rate of 11 nanomoles/g fungal mycelium/hour.

EXAMPLE 9

A 1 mM solution of thiophenol containing 0.2 mM chloromethane and buffered at pH 4.0 with 20 mM citrate buffer was incubated with 0.035 g of fungal mycelium (*Phellinus ribis* NCWRF. FPRL 42 or CBS 175.29) at a temperature of 25° C. for a period of 15 hours. Thioanisole was formed at a rate of 185 nanomoles/g fungal mycelium/hour.

EXAMPLE 10

The fungus *Phellinus lundelli* (CBS 540.72 obtained from the Centraalbureau voor Schimmelcultures, Baarn, The Netherlands) was used as a basis of the system.

A 2 mM solution of butyric acid containing 0.2 mM chloromethane and buffered at pH 4.0 with 20 mM citrate buffer was incubated with 0.035 g of fungal mycelium for a period of 15 hours at a temperature of 25° C. Methyl butyrate was formed at a rate of 97 nanomoles/g fungal mycelium/hour.

EXAMPLE 11

A 1 mM solution of thiophenol containing 0.2 mM chloromethane and buffered at pH 4.0 with 20 mM citrate buffer was incubated with 0.035 g of fungal mycelium (*Phellinus lundelli* (CBS 540.72)) at a temperature of 25° C. for a period of 15 hours. Thioanisole was formed at a rate of 45 nanomoles/g fungal mycelium/hour.

EXAMPLE 12

The fungus *Phellinus robiniae* (NCWRF-FPRL 180 obtained from the National Collection of Wood Rotting Fungi, Princes Risborough Laboratory, Building Research Establishment, Aylesbury, Bucks or CBS 211.36 obtained from the Centraalbureau voor Schimmelcultures, Baarn, The Netherlands) was used as a basis of the system.

A 2 mM solution of phenol containing 0.2 mM chloromethane and buffered at pH 4.0 with 20 mM citrate buffer was incubated with 0.035 g of fungal mycelium for a period of 15 hours at a temperature of 25° C. Anisole was formed at a rate of 8 nanomoles/g fungal mycelium/hour.

EXAMPLE 13

The fungus *Phellinus hippophaecola* (CBS 168.31 obtained from the Centraalbureau voor Schimmelcultures, Baarn, The Netherlands) was used as a basis of the system.

A 2 mM solution of butyric acid containing 0.2 mM chloromethane and buffered at pH 4.0 with 20 mM citrate buffer was incubated with 0.035 g of fungal mycelium for a period of 15 hours at a temperature of 25° C. Methyl butyrate was formed at a rate of 49 nanomoles/g fungal mycelium/hour.

EXAMPLE 14

The fungus *Phellinus tremulae* (CBS 123.40 obtained from the Centraalbureau voor Schimmelcultures, Baarn, The Netherlands) was used as the basis of the system.

A 2 mM solution of butyric acid containing 0.2 mM chloromethane and buffered at pH 4.0 with 20 mM citrate buffer was incubated with 0.035 g of fungal mycelium for a period of 15 hours at a temperature of 25° C. Methyl butyrate was formed at a rate of 26 nanomoles/g fungal mycelium/hour.

EXAMPLE 15

The fungus *Fomitopsis pinicola* (CBS 313.82 obtained from the Centraalbureau voor Schimmelcultures, Baarn, The Netherlands) was used as the basis of the system.

A 1 mM solution of benzoic acid containing 1.23 mM chloromethane and buffered at ph 4.0 with 20 mM citrate buffer was incubated with 0.035 g of fungal mycelium for a period of 15 hours at a temperature of 25° C. Methyl benzoate was formed at a rate of 6 nanomoles/g fungal mycelium/hour.

I claim:

1. A method of O-methylation of a phenol, S.-methylation of a thiophenol or methylesterification of a carboxylic acid comprising contacting the phenol, thiophenol or carboxylic acid with a halomethane in the presence of a fungus selected from a group consisting of Hymenochaetaceae, Polyporaceae and Corticiaceae.

2. A method as claimed in claim 1, wherein the fungus is selected from *Phellinus pomaceus*, (CBS 137.42), *Phellinus ribis* (CBS 175.29), *Phellinus lundelli* (CBS 540.72), *Phellinus robiniae* (CBS 211.36), *Phellinus hippophaecola* (CBS 168.31), *Phellinus tremulae* (CBS 123.40) and *Fomitopsis pinicola* (CBS 313.82).

3. A method as claimed in claim 1, wherein the reaction is carried out at a temperature of from 15° C. to 25° C.

4. A method as claimed in claim 1, wherein the pH of the reaction mixture is from 2 to 8.

5. A method as claimed in claim 1, wherein the halomethane is gaseous.

* * * * *